(12) United States Patent
DuRussel

(10) Patent No.: US 9,404,907 B2
(45) Date of Patent: Aug. 2, 2016

(54) COMPONENTS AND METHOD OF USE OF A HOME LIPSTICK LEAD TEST KIT

(71) Applicant: Katherine DuRussel, Reese, MI (US)

(72) Inventor: Katherine DuRussel, Reese, MI (US)

( * ) Notice: Subject to any disclaimer, the term of this patent is extended or adjusted under 35 U.S.C. 154(b) by 259 days.

(21) Appl. No.: 14/184,652

(22) Filed: Feb. 19, 2014

(65) Prior Publication Data
US 2015/0233886 A1 Aug. 20, 2015

(51) Int. Cl.
*G01N 21/78* (2006.01)
*G01N 21/77* (2006.01)
*G01N 33/20* (2006.01)
*G01N 33/52* (2006.01)
*G01N 21/84* (2006.01)

(52) U.S. Cl.
CPC ............... *G01N 33/20* (2013.01); *G01N 21/78* (2013.01); *G01N 21/77* (2013.01); *G01N 21/84* (2013.01); *G01N 33/52* (2013.01); *G01N 2021/7706* (2013.01); *G01N 2021/7759* (2013.01)

(58) Field of Classification Search
CPC ....... G01N 21/78; G01N 21/77; G01N 21/84; G01N 33/20; G01N 33/52; G01N 2021/7706; G01N 2021/7759
See application file for complete search history.

(56) References Cited

U.S. PATENT DOCUMENTS 6,489,170 B1 * 12/2002 Cole .................... G01N 31/22
436/73
2011/0283785 A1 * 11/2011 Askin .................. G01N 33/32
73/150 R

* cited by examiner

*Primary Examiner* — Jennifer Wecker

(57) ABSTRACT

Lipsticks are tested by a lead indicator solution. A lipstick is swiped across a sheet of wax paper, forming a lipstick sample. The test solution is applied, in droplet form, to the sample of lipstick, and allowed to sit for a period of time so a chemical change can occur in the solution, if there is lead present in the lipstick. A cotton swab is used to absorb the solution, and the tip of the swab picks up a bit of the lipstick sample. A color change is observed in the solution on the swab if lead is present in the lipstick. The amount of lead is determined by what color the solution changes to.

3 Claims, 4 Drawing Sheets

COMPONENTS AND METHOD OF USE OF A HOME LIPSTICK LEAD TEST KIT

CROSS-REFERENCE TO RELATED APPLICATIONS

N/A

TECHNICAL FIELD

The invention of this Home Lipstick Lead Test Kit uses simple techniques to test lipstick samples for lead content by the application of a test solution to a lipstick sample, allowing the solution to set for a period of time, absorbing the solution with a cotton swab, and observing a chemical change in the solution.

BACKGROUND OF THE INVENTION

Researchers and corporations have proven that lipsticks contain levels of lead through many different analytical techniques. The FDA has conducted their own research by: Hepp, N. M., "Determination of Total Lead in 400 Lipsticks on the U.S. Market Using a Validated Microwave-Assisted Digestion, Inductively Coupled Plasma—Mass Spectrometric Method," *Journal of Cosmetic Science*, accepted for publication in May/June, 2012, issue. Their research showed lipsticks could contain up to 7.19 ppm lead. To compare, tolerance levels for lead in water and candy are zero and 0.1 ppm, making the levels in lipstick concerning. This home test kit was developed so that consumers can determine if their lipsticks are safe to use.

There are other home lead test kits available on the market, but the techniques and/or indicators these tests use do not work on lipsticks. Either the solution is applied in a manner that the lipstick color interferes with indication (rubbing the solution indicator on the lipstick), or the lead indicator itself changes to a color similar to that of the lipstick. This lipstick lead test kit was designed specifically to work on lipsticks and give accurate results.

BRIEF SUMMARY OF THE INVENTION

This Home Lipstick Lead Test Kit is specifically designed to give accurate and safe results for the testing of lipsticks for lead. The concentration of the testing solution has been made to be as safe as possible, and the method of testing is designed specifically for lipsticks; unlike other tests, this method avoids the contamination of the lipstick with the solution, and allows for accurate color change to be observed, whereas other tests allow the color of the lipstick color to interfere with lead indication. Other tests apply their solution with an absorbent swab to the substance being tested. Such tests don't work on lipsticks due to the transferable lipstick color.

This invention, by applying the solution first, allowing the solution to sit, and then absorbing the solution without mixing it with the lipstick, allows for a color change to be observed without interference of the lipstick. The purpose of this invention is to help lipstick users know if the product they're using is potentially toxic; a large majority of lipsticks have been proven to have testable levels of lead.

DETAILED DESCRIPTION OF THE INVENTION

Figure 2A:
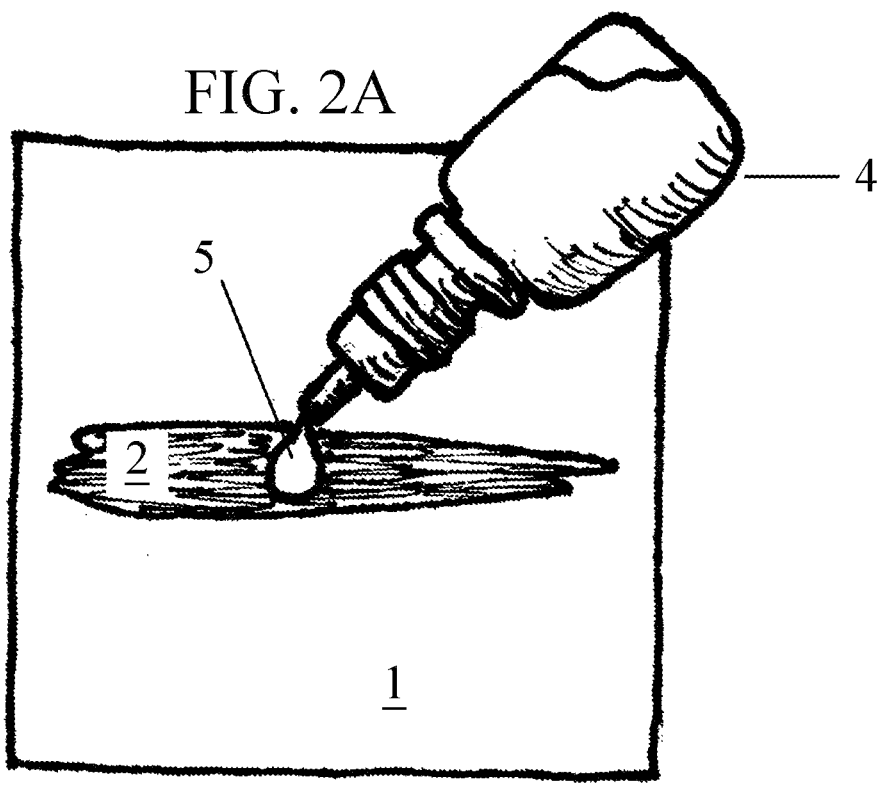
FIG. 2A-2B illustrates the application of the test solution in droplet form by an eyedropper bottle.
Figure 2B:
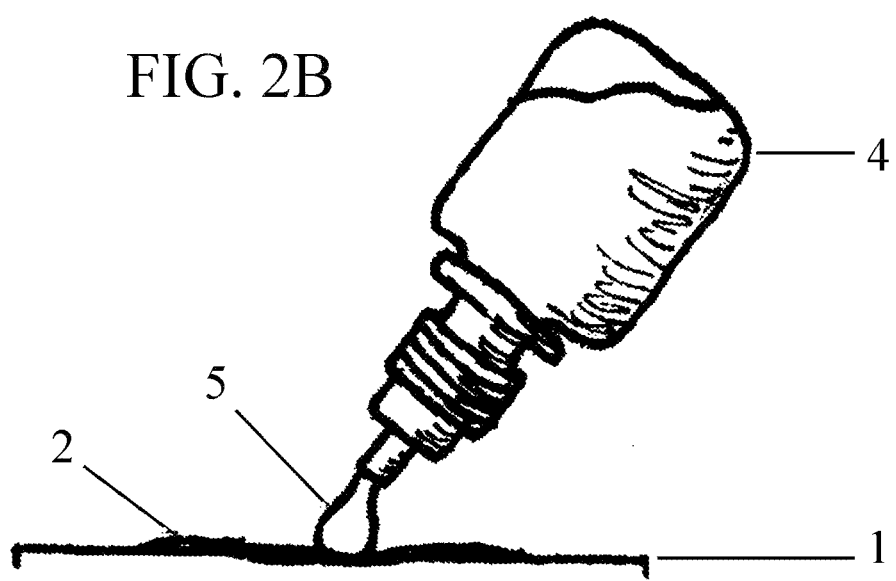

Development: 2.5 g of sodium sulfide (lead indicator) were measured by weight on a scale. The 2.5 g of sodium sulfide were mixed by inversion with 50 mL of distilled water in a volumetric flask. This formed the sodium sulfide test solution with a concentration of 1:20. The solution is clear in the absence of lead, but when the solution comes in contact with lead, it forms a lead nitrate that ranges in color from light yellow to black/brown; black/brown indicates high lead content, and light yellow indicates low lead content. The solution was transferred from the flask to a sealed eyedropper bottle (bottle shown in FIG. 2A-2B, reference #4).

Figure 1:
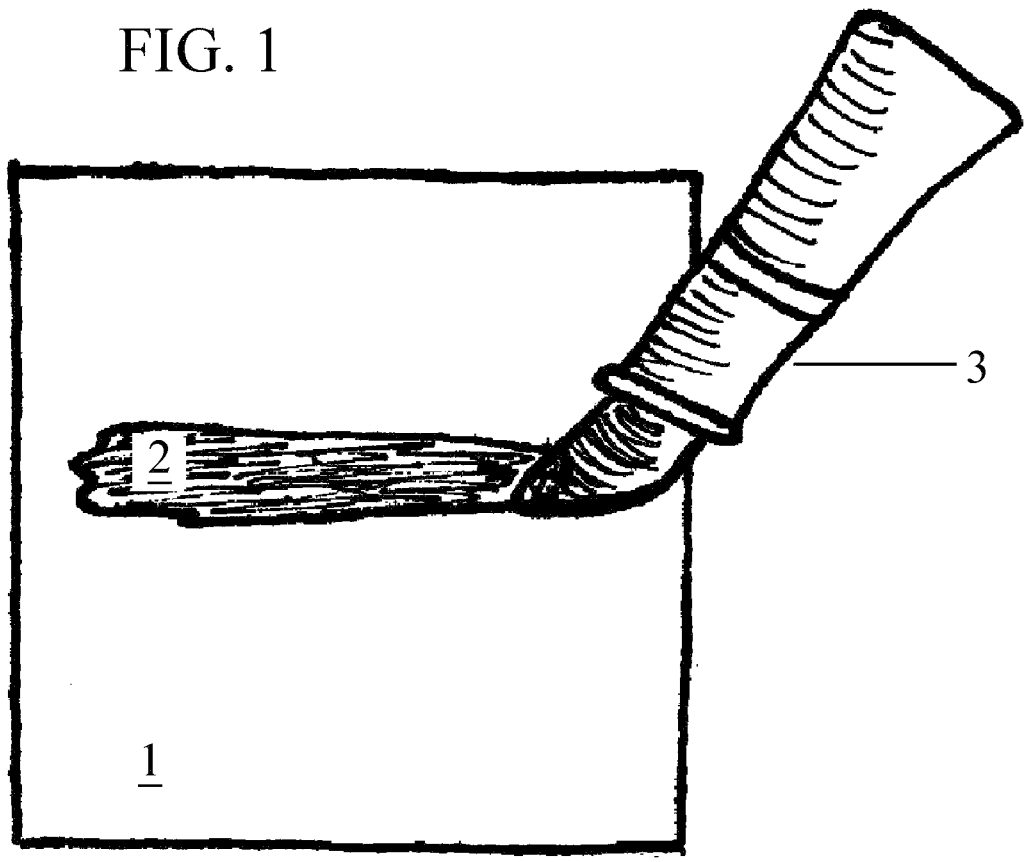
FIG. 1 illustrates the application of the lipstick being tested to a sheet of wax paper.

Method of Testing Lipsticks for Lead: (FIG. 1) Swipe the lipstick being tested (3) across a sheet of wax paper (1) so that there is a thin streak (2) of lipstick on the paper (1). This streak (2) will be referred to as the lipstick sample.

(FIG. 2A-2B) Apply a drop (5) of the sodium sulfide test solution contained in an eyedropper bottle (4) to the lipstick sample (2). Let the drop of solution (5) sit on the lipstick sample (2) for one minute.

Figure 3A:
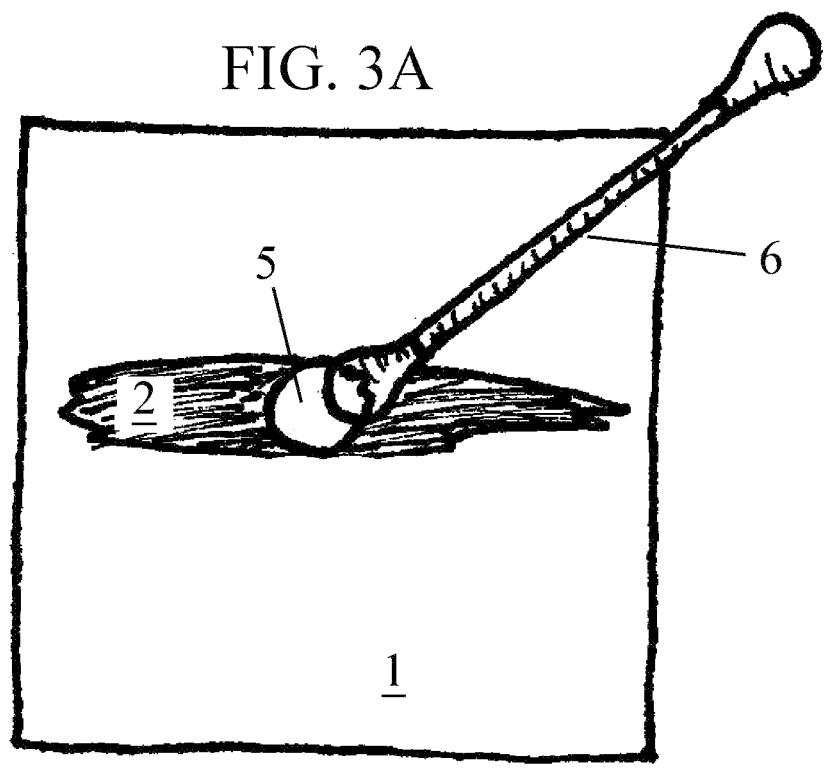
FIG. 3A-3B illustrates the absorption of the solution by a cotton swab.
Figure 3B:
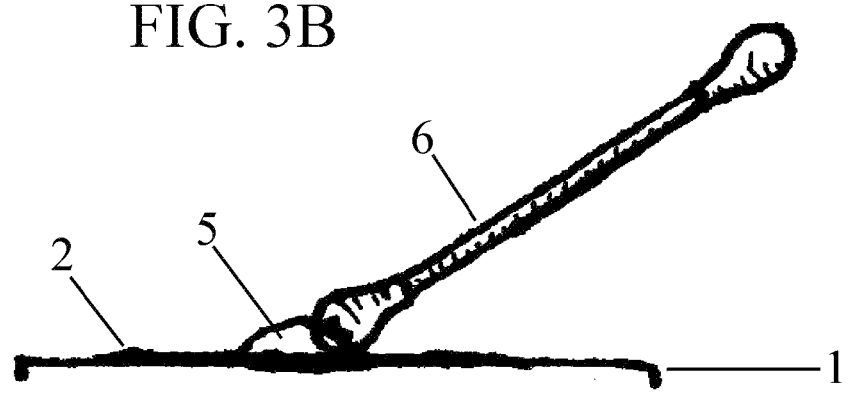

(FIG. 3A-3B) Use a solid stemmed, absorbent ended, cotton swab (6) to absorb the drop of solution (5). Allow the tip of the cotton swab (6) to pick up an extremely small of the lipstick sample (2) while absorbing the solution (5). The lipstick is picked up due to the fact that it has been exposed to the solution for a long time, and will help in indication. However, only an extremely small amount should be allowed on the swab, otherwise the lipstick color would interfere with lead indication.

Figure 4:
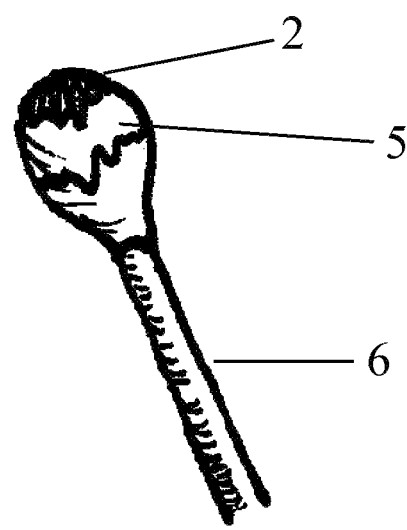
FIG. 4 illustrates the final view of the cotton swab with solution and lipstick on it.

FIG. 4 depicts what the cotton swab (6) should look like after absorbing the solution (5) and picking up a bit of lipstick (2). A color change (formation of a lead nitrate) can be observed in the solution (5) surrounding the lipstick (2) on the cotton swab (6). It is important that very little lipstick is on the swab.

In some cases, extremely bright lipstick color can leach into the solution droplet. If this occurs, retest the lipstick using the same method, but reduce the time that the solution droplet sits on the lipstick sample to twenty seconds. This method works, but it is preferable to let the solution sit for one minute for ultimate accuracy.

The invention claimed is:

1. A method of testing lipsticks for lead content comprising:
    swiping a lipstick across a sheet of wax paper;
    applying a sodium sulfide test solution, in droplet form, on the sample swipe of lipstick by use of a sealed eyedropper bottle;
    allowing the solution to set on the lipstick swipe for one minute; absorbing the solution with a solid stemmed, absorbent ended, cotton swab;
    allowing the tip of the cotton swab to pick up an extremely small amount of the lipstick sample while absorbing the test solution;
    and determining lead presence by observing a change in the color of the solution on the cotton swab, wherein said sodium sulfide test solution is colorless in the absence of lead, and wherein when the test solution comes in contact with lead, it forms a lead nitrate that ranges in color from light yellow to black/brown, wherein black/brown indicates high lead content, and light yellow indicates low lead content.

2. The method described in claim 1, wherein the solution is absorbed twenty seconds after application.

3. The sodium sulfide test solution of claim 1, comprising a concentration ratio of 1:20, or one part sodium sulfide to twenty parts distilled water.

\* \* \* \* \*